Figure 1:
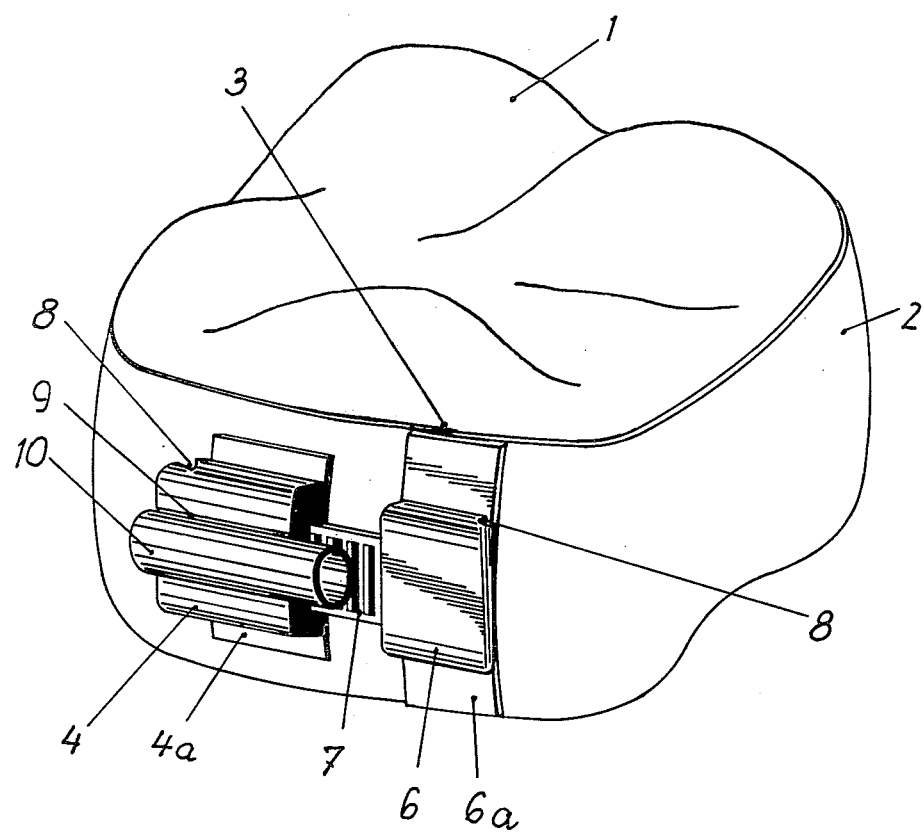

United States Patent [19]

Förster

[11] 4,198,753
[45] Apr. 22, 1980

[54] DENTAL FIXING ELEMENT

[75] Inventor: Rolf Förster, Pforzheim, Fed. Rep. of Germany

[73] Assignee: Firma Bernhard Förster, Pforzheim, Fed. Rep. of Germany

[21] Appl. No.: 881,380

[22] Filed: Feb. 27, 1978

Related U.S. Application Data

[63] Continuation-in-part of Ser. No. 792,193, Apr. 29, 1977, Pat. No. 4,167,813.

[30] Foreign Application Priority Data

Mar. 26, 1977 [DE] Fed. Rep. of Germany ....... 2713446

[51] Int. Cl.² ............................................. A61C 7/00
[52] U.S. Cl. ......................................... 433/8; 433/10; 433/23
[58] Field of Search .......... 24/255 SL, 206 A, 16 PB, 24/20 TT; 32/14 A, 62, 63, 66; 81/345, 355, 373, 129

[56] References Cited

U.S. PATENT DOCUMENTS

| | | | |
|---|---|---|---|
| 2,007,517 | 7/1935 | Boyd et al. | 32/14 A |
| 2,104,192 | 1/1938 | Ford | 32/14 A |
| 2,979,794 | 4/1961 | Bartolo | 24/206 A |
| 3,115,200 | 1/1964 | Bell | 24/206 A |
| 3,138,872 | 6/1964 | Lazarus | 32/14 A |
| 3,900,923 | 8/1975 | Thomas | 24/206 A |
| 3,913,187 | 10/1975 | Okuda | 24/255 |
| 3,922,787 | 12/1975 | Fischer et al. | 32/14 A |

Primary Examiner—Russell R. Kinsey
Assistant Examiner—Michael J. Foycik, Jr.

[57] ABSTRACT

The element is adapted to be fitted as an annular band around a tooth and to be secured to a dental appliance to hold the same in position. It includes a strip metal element having two end portions, which are adapted to overlap in the annular band, a first slide-snap fastener part, which is carried by one of the end portions and includes a tunnel member defining a tunnel passage extending longitudinally of the strip metal element, and a detent spring secured to the tunnel member and extending longitudinally in the passage, a second slide-snap fastener which is carried by the other of the end portions and includes a plurality of barblike oblique detent teeth spaced apart in the longitudinal direction of the strip metal element and movable relative to the first fastener part in a closing direction into the tunnel passage. At least part of the detent spring protrudes transversely into the passage generally at an acute angle to the closing direction and is selectively interengageable with the detent teeth in a plurality of positions, which determine respective diameters of the annular band.

15 Claims, 9 Drawing Figures

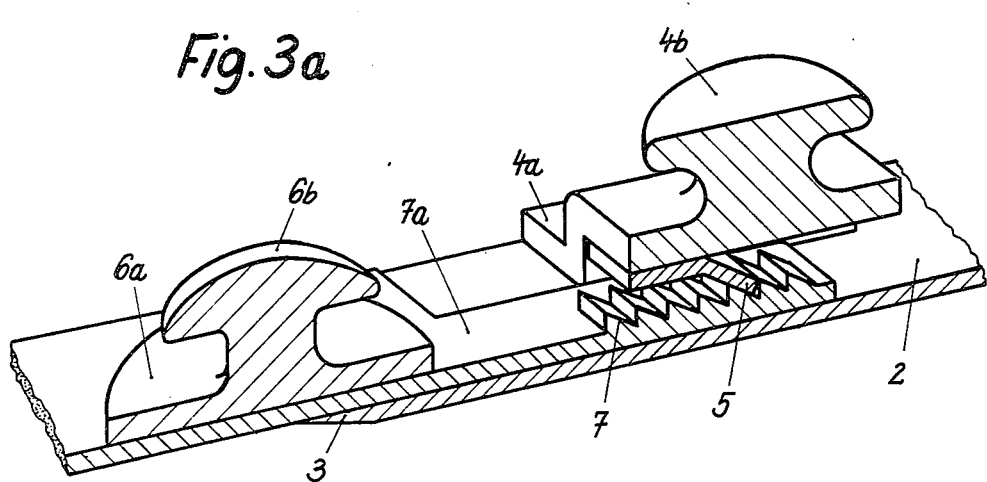
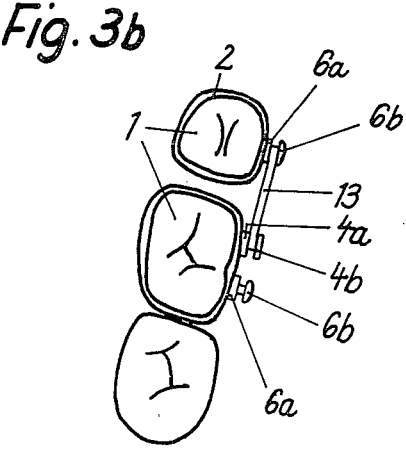

DENTAL FIXING ELEMENT

This application is a continuation in part of Ser. No. 792,193 filed 4/29/77, now U.S. Pat. No. 4,167,813, patented 9/18/79.

This invention relates to an adjustable strip metal element for dental purposes, specifically for use as an adjustable fixing and supporting element, which is intended to be fitted around a tooth and to be connected to an orthodontic or prosthetic appliance to hold it in position.

An element of that kind described in U.S. Patent Application Ser. No. 792,193 filed Apr. 29, 1977, has end portions provided with bevelled surfaces for forming a scarfed joint and with slide-snap fastener parts. Owing to the geometric configuration of the known strip metal element, the fastener is disposed on the mouth side in a lingual position relative to that tooth surface which faces the tongue. When the element is fitted around a molar tooth, which is rectangular, there is sufficient space for accommodating the slide-snap fastener. Incisors have a configuration which is similar to an ellipse, one radius of which is buccal and the other lingual relative to the cheek. At relatively small teeth, the space which is available on the lingual side is hardly sufficient for accommodating a slide-snap fastener. In the use of the known strip metal element it is also difficult to apply the force required to close the slide-snap fastener in the patient's mouth.

A main object of the invention is to provide a strip metal element which is of the kind described in the above-mentioned prior application and has an improved slide-snap fastener, which can be disposed on the lingual side as well as on the buccal side and which can also be closed more easily and can be combined with retaining elements, if this is desired.

In a strip metal element which is of the kind described first hereinbefore and has end portions provided with slide-snap fastener parts and preferably with bevelled surfaces for forming a scarfed joint, this object is accomplished according to the invention in that a tunnel member is provided on one strip end portion and has at its end a detent spring which is laterally bent in the direction of movement of the other strip end portion as the latter enters the tunnel member, whereas the other strip end portion comprises oblique barblike detent teeth for a snap engagement with the detent spring, which yields as said other strip end portion is moved into the tunnel member, so that an adjustable slide-snap fastener is obtained. Each strip end portion is preferably provided with a raised abutment, which has an undercut for engagement by a forceps as the fastener parts are fitted one into the other. One of said abutments constitutes the tunnel member and the other abutment holds a detent bar.

According to another feature of the invention, the strip metal element is provided with a plurality of buttons, each of which has an enlarged base portion mounted on an associated strip end portion and an enlarged head portion opposite to the base portion in an arrangement in which one base portion is preferably formed with a tunnel passage provided with a detent leaf spring for interlocking with detent teeth provided on the other strip end portion. Strip metal elements provided with such buttons may be applied to two or more teeth which are to be corrected by elastic strips laid around the buttons.

Figure 2:
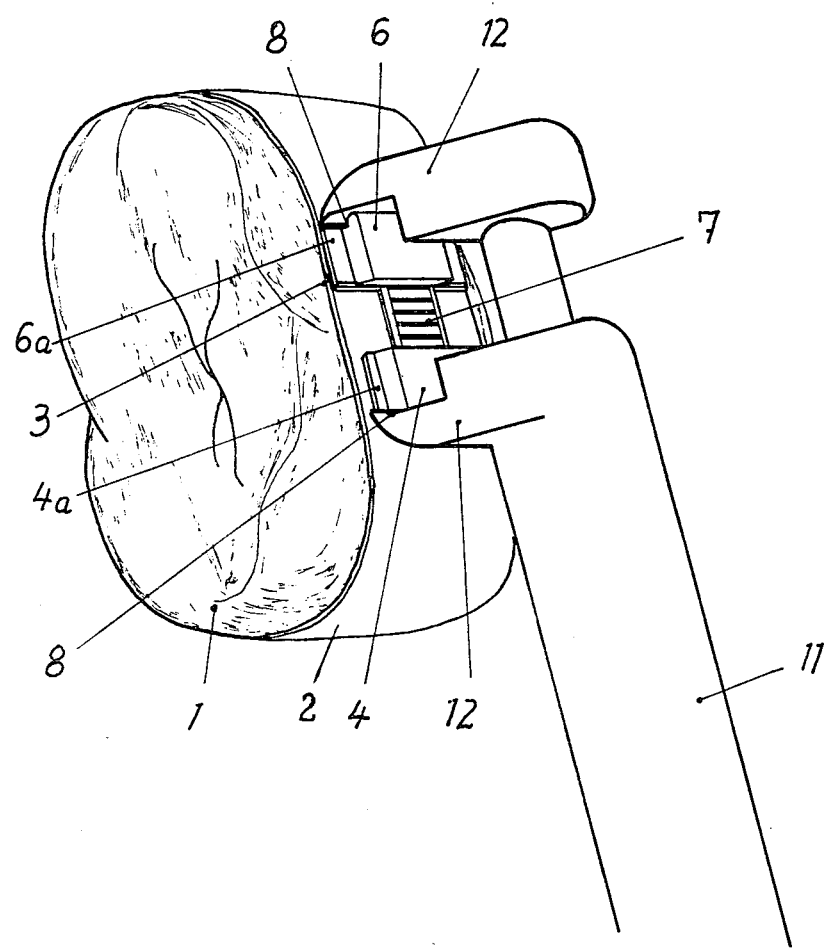
Figure 3:
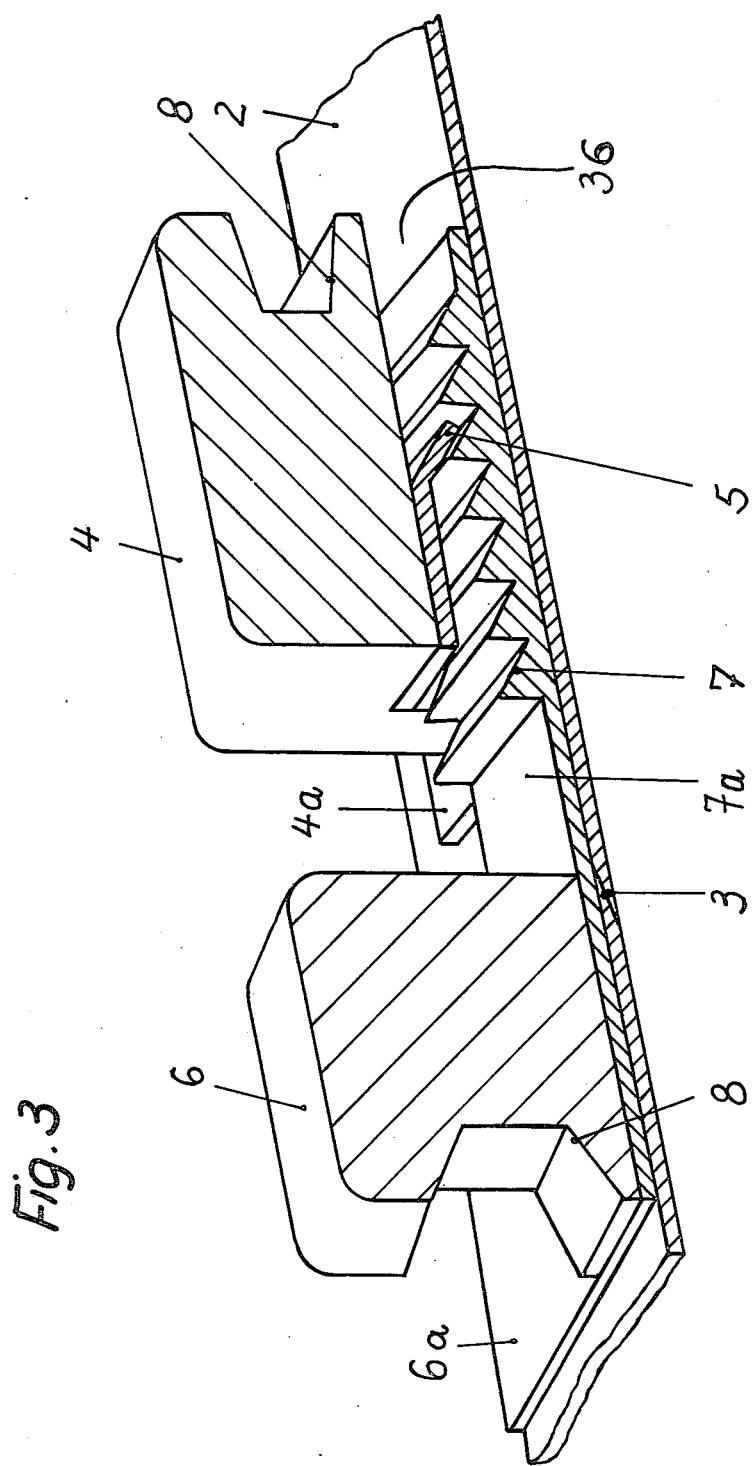
Figure 4:
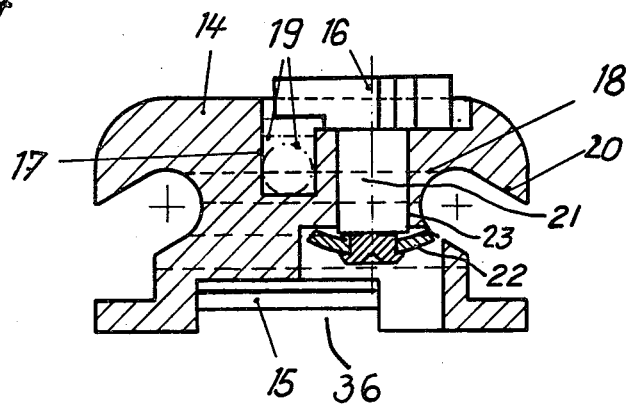
Figure 5:
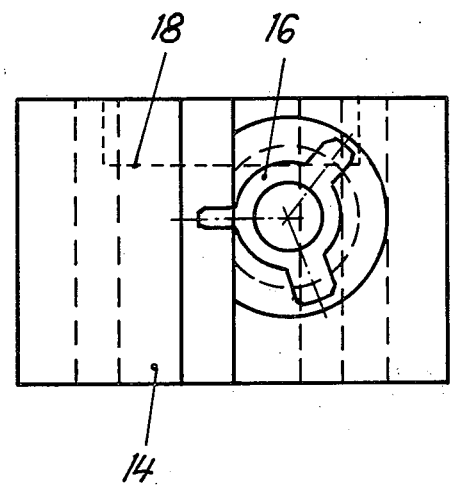
Figure 6:
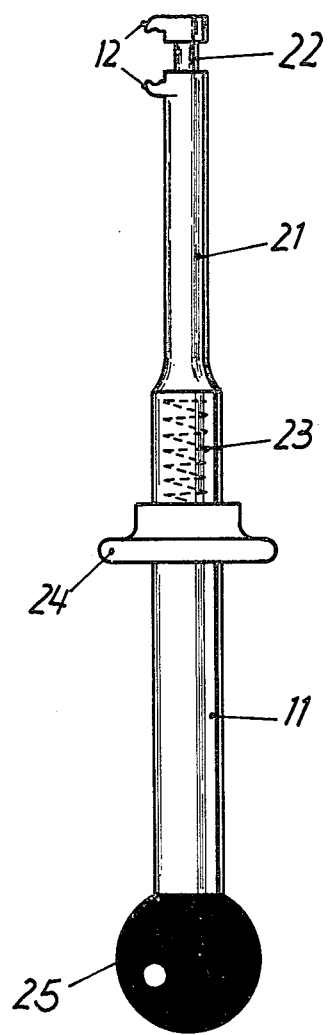
Figure 7:
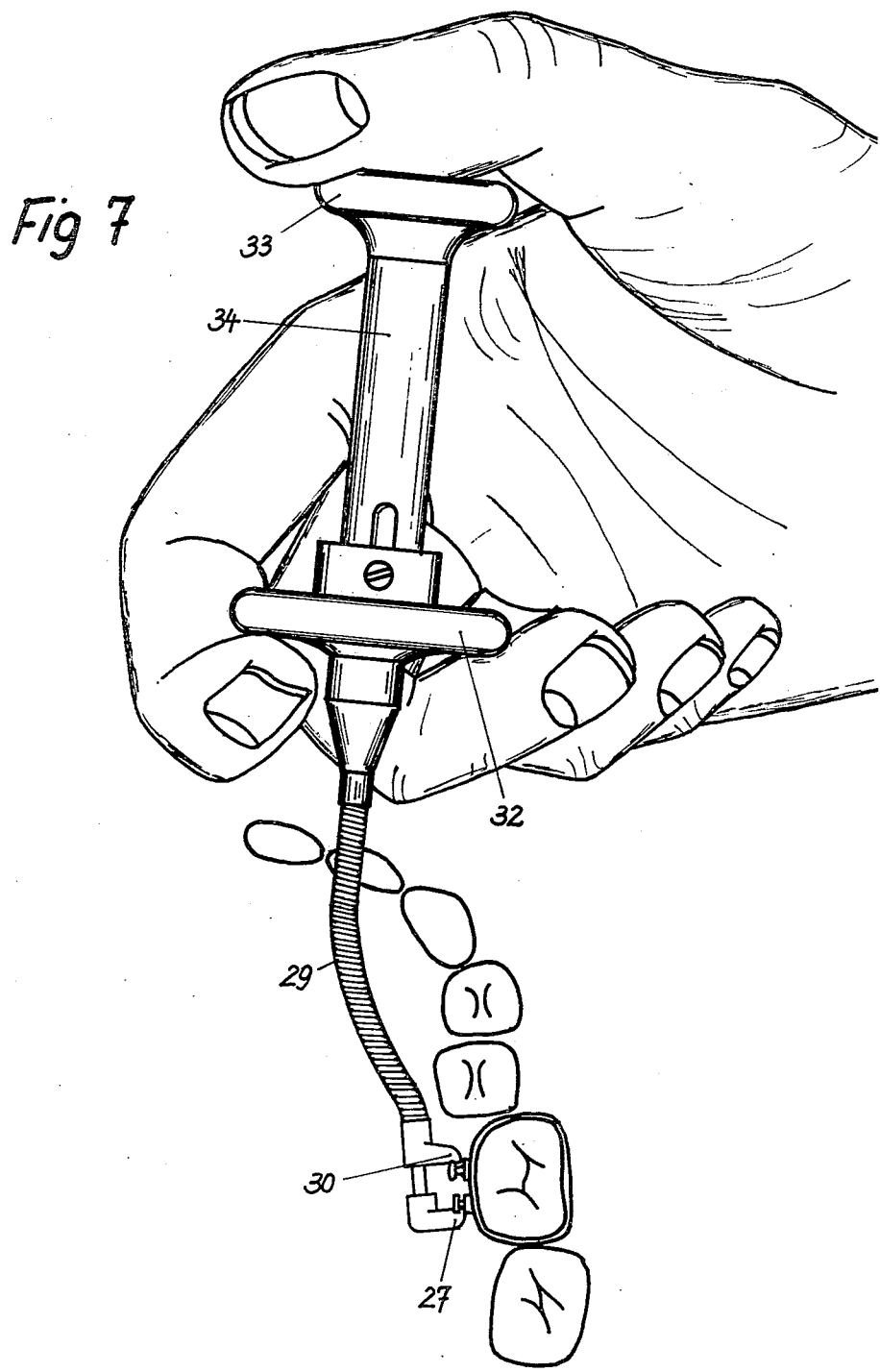

Further details of the invention will be described hereinafter with reference to embodiments shown by way of example on the accompanying drawings, in which FIG. 1 is a perspective view showing a first embodiment of a strip metal element which is provided with a slide-snap fastener and applied around a tooth, FIG. 2 is a perspective view showing a second embodiment of a strip metal fastener which is provided with a slide-snap fastener and has been applied around a tooth and is being tightened, FIG. 3 is a perspective central sectional view showing on a still larger scale than the preceding figures a strip metal element provided with a slide-snap fastener, FIGS. 3a and 3b are enlarged perspective central sectional views showing another embodiment of a metal strip element provided with a slide-snap fastener and the use of that embodiment for tooth correction, FIGS. 4 and 5 are, respectively, a sectional view and a top plan view showing a slide-snap fastener part which constitutes a bracket, FIG. 6 is an elevation showing a forceps for tightening the fastener shown in FIGS. 4 and 6, and FIGS. 7 and 8 are, respectively, an elevation and a sectional view showing another forceps, which is shown in FIG. 7 in position for use.

FIG. 1 shows a strip metal element 2 which is to be applied around a tooth 1 and has a scarfed joint 3 formed by bevelled end portions. The strip end portions carry respective abutments 4 and 6, which constitute fastener parts and comprise respective baseplates 4a and 6a welded to the strip metal element. The fastener part 4 constitutes a tunnel member, which is provided with a laterally bent detent spring 5, which is shown in FIG. 3. The other fastener part 6 is provided with a tongue 7a having detent teeth 7, which interengage with the detent spring 5 in the tunnel passage 36 of the tunnel member 4 as shown in FIG. 3. Each of the fastener parts 4 and 6 has an undercut 8 for engagement by a forceps as shown in FIG. 2. It is apparent from FIG. 1 that the tunnel member 4 has in its surface remote from the strip metal element 2 a longitudinal recess 9 for receiving retaining or anchoring elements, which are soldered to the tunnel member and may consist, e.g., of a tubular member 10 for tooth-correcting strips or wires.

FIG. 2 shows a strip metal element 2 which has been applied around a tooth 1 and has a scarfed joint formed by bevelled end portions 3, which are respectively provided with fastener parts 4 and 6 having baseplates 4a and 6a, respectively, which are welded to the strip metal element. The fastener part 4 constitutes a tunnel member, which is provided in its tunnel passage with a laterally bent detent spring 5, which is shown in FIG. 3. The other fastener part 6 is provided with a serrated detent bar 7, which cooperates with the tunnel member 4 as a slide-snap fastener. To close the fastener, a forceps 11 may be used, which has two relatively slidable gripping jaws 12 for engaging undercuts 8 of the parts 4 and 6.

FIG. 3 is a sectional view showing the strip metal element 2 forming a scarfed joint 3 and provided with a tunnel member 4, which has in its tunnel passage 36 a laterally bent detent spring 5, and a second fastener part 6 provided with a tongue 7a having detent teeth 7, which can be caused to interengage with the detent spring 5 by means of a forceps, which engages with the undercuts 8.

FIG. 3a is a sectional view showing a strip metal element 2 which forms a scarfed joint 3 and is provided with fastener parts consisting of buttons, each of which comprises an enlarged base portion 4a or 6a and an enlarged head portion 4b or 6b and a neck portion between the base and head portions. The base portion 4a, 4b provided on one strip end portion constitutes a tunnel member and is formed in its base portion 4a with a tunnel passage 36, in which a laterally bent leaf spring 5 extends, which interengages with detent teeth 7 of a tongue 7a with which the second strip end portion is provided. Each of these buttons mounted on the end portions of strip metal elements 2 applied around teeth 1 or may be used for a correction of teeth by means of elastic strips 13 applied around the button between its enlarged head and base portions. These buttons are so small that they may be disposed on the inside of teeth and may be used for instance, for turning molar teeth 1 and for other purposes.

FIGS. 4 and 5 show a fastener part 14 which consists of a tunnel member and is provided in its tunnel passage 36 with a laterally bent detent spring 15. The tunnel member 14 cooperates with a fastener part 6, which is of the type described hereinbefore and provided with a serrated detent bar 7. In the present embodiment, the tunnel member 4 consitutes also a bracket. The bracket may be provided with a longitudinal groove 17 for slidably receiving an orthodontic appliance, and with a clamping device 16, which projects over said groove and is selectively angularly movable to positions for slidable and clamping engagement, respectively, with an orthodontic appliance 19 received in said groove so that the clamping device 16 is adapted to secure said bracket to said orthodontic appliance 19 in a selected position. The clamping device 16 may comprise a rotatable plate, which has portions differing in thickness and protruding over said groove 17, or may comprise a plurality of radial clamping arms, which differ in thickness and are angularly spaced apart, each of said arms being selectively angularly movable to a position in which it protrudes over said groove 17. The bracket may also comprise laterally disposed, longitudinally extending grooves defined by shoulders 20 and adapted to receive tying elements for securing orthodontic arches as has been described in the above-mentioned application. In this embodiment, one and the same member serves both as a bracket and as part of the fastener and also, on the bracket end, for the connection of a tying wire to a tooth without need for additional means for fixing the tying wire. In the embodiment shown, the combined tunnel-and-bracket member 14 has also an undercut 18 for engagement by a forceps 11.

As shown in FIG. 4, the clamping device 16 may be rotatably mounted in the bracket by means of a rotatable stub shaft 21, the clamping device 16 axially fixed to the shaft 21. A snubbing spring 22, curved toward the bracket, is riveted to the free end of shaft 21 and tends to hold the same and the clamping device 16 in a predetermined axial position relative to the bracket. On the other side or opposite side of longitudinal groove 17, the bracket is provided with a transversing recess 23 for receiving shaft 21. Recess 23, at its lower end, communicates with tunnel passage 36.

Clamping device 16 is disposed above the upper part of recess 23, and snubbing spring 22 is disposed at the lower end of recess 23.

FIG. 6 shows the forceps 11 having two gripping jaws 12, which are displaceable relative to each other. One gripping jaw 12 is carried by a tube 21, which slidably surrounds a rod 22 carrying the other jaw 12. The rod 22 is surrounded by a spring 23, which urges the gripping jaws 12 axially apart. The forceps 11 is provided with a ring member 24 and with a ball end 25, which are axially movable relative to each other to move the gripping jaws 12 towards each other against the force of the spring 23 so that the fastener consisting of the members 4 or 14, on the one hand, and 6, on the other hand, can be closed. This enables a simple fixation of the strip metal element 2 around the tooth 1 by means of the slide-snap fastener.

Figure 8:
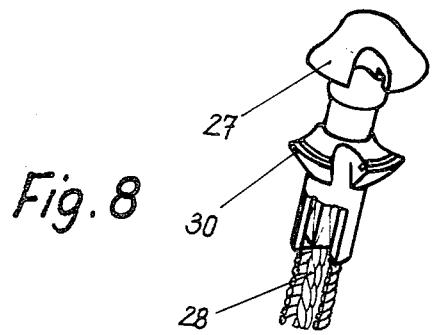
Figure 8:
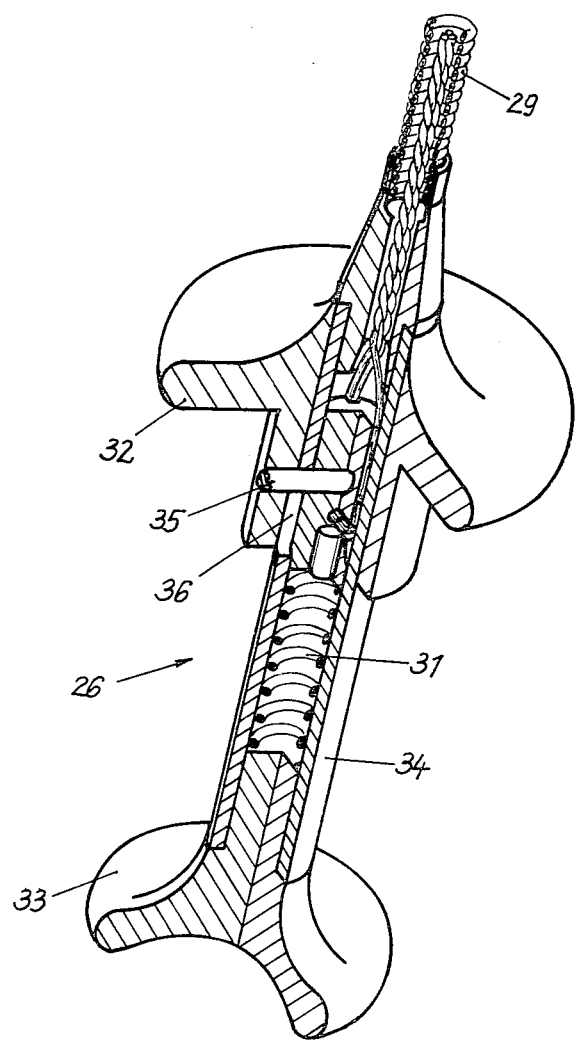

Another forceps 26 is shown in FIGS. 7 and 8 and comprises a gripping jaw 27, which is movable toward the second gripping jaw 30 against the force of a spring 31 by means of a cable 28 extending in a flexible metal tubing 29, which is connected to the gripping jaw 30, whereas the cable 28 is connected to the gripping jaw 27 and to a finger ring 32, which is displaceable against the force of the spring 31. The flexible metal tubing 29 is connected to a head member 33 by a guide tube 34, on which the finger ring 32 is fitted. The latter carries a pin 34, which extends in a slot 35 of the guide tube 34 so that the parts 32 and 34 are axially slidable relative to each other within limits defined by a pin-slot joint 34, 35. The spring 31 tending to return the finger ring 32 is accommodated in the guide tube 34, as is apparent from the sectional view of FIG. 8.

What is claimed is:

1. A dental fixing element which is adapted to be fitted as an annular band around a tooth and to be secured to a dental appliance to hold the same in position, comprising a strip metal element having two end portions, which are adapted to overlap in said annular band, a first slide-snap fastener part, which is carried by one of said end portions, a second slide-snap fastener part which is carried by the other of said end portions, each of said fastener parts being formed with an undercut which is engageable by a suitable forceps, said first slide fastener part comprising an abutment member which includes a tunnel body defining a tunnel passage extending longitudinally of said strip metal element, and a detent spring secured to said tunnel body and extending longitudinally in said passage, said tunnel body being formed in its surface that is remote from said strip metal element with a longitudinally extending recess, said second slide-snap fastener part comprises an abutment member which includes a bar held by said abutment member, said bar having a plurality of barblike oblique detent teeth spaced apart in the longitudinal direction of said strip metal element and movable relative to said first fastener part in a closing direction into said tunnel passage, said detent teeth adapted to selectively interenage with said detent spring in said tunnel passage, in positions which determine respective diameters of said annular band, and a tubular member for receiving tooth correcting strips, disposed within said longitudinally extending recess, said detent spring protruding transversely within said passage, generally at an acute angle to said closing direction and being selectively interengageable with said detent teeth in a plurality of positions, by means of a suitable forceps engaging respective undercuts and operable to move said detent teeth in said closing direction relative to said first fastener part.

2. A dental fixing element as set forth in claim 1, which comprises means for securing the fixing element to an orthodontic appliance.

3. A dental fixing element as set forth in claim 1, which comprises means for securing the fixing element to a prosthetic appliance.

4. A dental fixing element as set forth in claim 1, in which teeth of said end portions has a bevelled surface, which is arranged to contact the other of said end portions when said end portions overlap in said annular band.

5. A dental fixing element as set forth in claim 1, in which said second fastener part is formed in its surface that is remote from said strip metal element with a longitudinally extending recess.

6. A dental fixing element as set forth in claim 1, in which said detent spring is a leaf spring, which near its rear end in said closing direction is welded to said tunnel member in said passage and which at its forward end in said closing direction extends at an acute angle to said closing direction.

7. A dental fixing element as set forth in claim 1, in which said tunnel body is formed on both sides with longitudinal grooves for receiving tying means for securing said dental appliance to said tunnel member.

8. A dental fixing element which is adapted to be fitted as an annular band around a tooth and to be secured to a dental appliance to hold the same in position, comprising
 a strip metal element having two end portions, which are adapted to overlap in said annular band,
 a first slide-snap fastener part, which is carried by one of said end portions and comprises a tunnel body defining a tunnel passage extending longitudinally of said strip metal element, and a detent spring secured to said tunnel body and extending longitudinally in said passage,
 a second slide-snap fastener part which is carried by the other of said end portions and comprises a plurality of barblike oblique detent teeth spaced apart in the longitudinal direction of said strip metal element and movable relative to said first fastener part in a closing direction into said tunnel passage,
 said detent spring protruding transversely into said passage generally at an acute angle to said closing direction and being selectively interenageable with said detent teeth in a plurality of positions, which determine respective diameters of said annular band,
 said fixing element comprising at least one button member which is carried by said strip metal element and has an enlarged base portion secured to said strip metal element and an enlarged head portion opposite to said base portion and is adapted to receive between said base and head portions a dental appliance consisting of an elastic strip for orthodontic purposes.

9. A dental fixing element as set forth in claim 8, in which each of said fastener parts comprises a button member having an enlarged base portion secured to one end portion of said strip element and an enlarged head portion opposite to said base portion, and each of said button members adapted to receive elastic strips around the periphery thereof between said base and head portions, for orthodontic purposes.

10. A dental fixing element as set forth in claim 9, in which one of said button members constitutes said tunnel body and is formed in its base portion with said tunnel passage.

11. A dental fixing element which is adapted to be fitted as an annular band around a tooth and to be secured to a dental appliance to hold the same in position, comprising
 a strip metal element having two end portions which are adapted to overlap in said annular band,
 a first slide-snap fastener part which is carried by one of said end portions,
 a second slide-snap fastener part which is carried by the other of said end portions,
 each of said fastener parts being formed with an undercut which is engageable by a suitable forceps,
 said first slide-snap fastener part comprises an abutment member which includes a tunnel body and a bracket, integral with each other, said tunnel body defining a tunnel passage extending longitudinally of said strip metal element, and a detent spring secured to said tunnel body and extending longitudinally in said passage,
 said bracket being formed on one side with a transversing recess, communicating with said tunnel passage, and on the other side thereof with a longitudinal groove for slidably receiving an orthodontic appliance,
 said bracket carrying a clamping device, which projects over said groove and is selectively angularly movable to positions for slidable and clamping engagement, respectively, with an orthodontic appliance received in said groove, so that the clamping device is adapted to secure said bracket to said orthodontic appliance in a selected position,
 a rotatable shaft axially fixed to the clamping device is disposed in said transversing recess, the clamping device rotatably mounted in said bracket by means of said shaft,
 means for securing said shaft in said bracket so as to locate said clamping device in a predetermined position relative to said bracket,
 said second slide-snap fastener comprises an abutment member which includes a bar held by said abutment member, said bar having a plurality of barblike oblique detent teeth spaced apart in the longitudinal direction of said strip metal element, and removable relative to said first fastener part, in a closing direction into said tunnel passage, said detent teeth adapted to selectively interengage with said detent spring in said tunnel passage, in positions which determine respective diameters of said annular band,
 said detent spring protruding transversely in said passage, generally at an acute angle to said closing direction, and being selectively interengageable with said detent teeth in a plurality of positions by means of a suitable forceps engaging respective undercuts and operable to move said detent teeth in said closing direction relative to said first fastener part.

12. A dental fixing element as set forth in claim 11, in which said clamping device comprises a rotatable plate, which has portions differing in thickness and protruding over said groove.

13. A dental fixing element as set forth in claim 11 in which said clamping device comprises a plurality of radial clamping arms which differ in thickness and are angularly spaced apart and each of said arms is selectively angularly movable to a position in which it protrudes over said groove.

14. A dental fixing element as set forth in claim 10, in which said bracket is formed on both sides with longitudinal grooves for receiving tying means for securing said dental appliance to said bracket.

15. A dental fixing element as set forth in claim 11, in which said shaft extends through said bracket, and said securing means comprise a spring disposed in said transversing recess and curved toward said bracket for securing, said shaft in said bracket in a predetermined axial position.

* * * * *